(12) United States Patent
Norebring

(10) Patent No.: US 10,092,700 B2
(45) Date of Patent: Oct. 9, 2018

(54) MEDICAMENT DELIVERY DEVICE

(71) Applicant: Carebay Europe Ltd, Swatar (MT)

(72) Inventor: Jonas Norebring, Stockholm (SE)

(73) Assignee: Carebay Europe Ltd, Sliema (MT)

( * ) Notice: Subject to any disclaimer, the term of this patent is extended or adjusted under 35 U.S.C. 154(b) by 849 days.

(21) Appl. No.: 14/385,161

(22) PCT Filed: Mar. 7, 2013

(86) PCT No.: PCT/EP2013/054577
§ 371 (c)(1),
(2) Date: Sep. 14, 2014

(87) PCT Pub. No.: WO2013/135549
PCT Pub. Date: Sep. 19, 2013

(65) Prior Publication Data
US 2015/0047631 A1    Feb. 19, 2015

Related U.S. Application Data

(60) Provisional application No. 61/612,012, filed on Mar. 16, 2012.

(30) Foreign Application Priority Data

Mar. 16, 2012   (SE) ........................ 1250249

(51) Int. Cl.
*A61M 5/28*   (2006.01)
*A61M 11/06*  (2006.01)
(Continued)

(52) U.S. Cl.
CPC .............. *A61M 5/284* (2013.01); *A61M 5/24* (2013.01); *A61M 5/31511* (2013.01);
(Continued)

(58) Field of Classification Search
CPC .... A61M 11/00; A61M 11/007; A61M 11/06; A61M 11/08; A61M 3/005;
(Continued)

(56) References Cited

U.S. PATENT DOCUMENTS 2,591,046 A * 4/1952 Brown ................. A61M 5/284
                                                222/136
4,613,326 A    9/1986 Szwarc
(Continued)

FOREIGN PATENT DOCUMENTS

CN    1165039 A    11/1997
EP    0671179 A2    9/1995
(Continued)

OTHER PUBLICATIONS

EPO, Int'l Search Report in PCT/EP2013/054577, dated Jul. 16, 2013, pp. 1-4.
(Continued)

*Primary Examiner* — Jackie Tan-Uyen T Ho
*Assistant Examiner* — Joseph D Boecker
(74) *Attorney, Agent, or Firm* — Piedmont Intellectual Property

(57) ABSTRACT

A medicament delivery device for a disposable container having at least one chamber for a liquid medicament encapsulated in the container by at least one movable plunger. The medicament delivery device is elongated along a longitudinal axis (A), has proximal and distal ends, and includes a housing with proximal housing section configured for accommodating the disposable container and a distal housing section; a plunger rod configured for contacting the movable plunger; and a drive mechanism arranged in the distal housing section for applying, when the medicament delivery device is activated, a force on the movable plunger in a proximal direction via the plunger rod. The plunger rod
(Continued)

includes an outer periphery having at least two axially separated recesses or cut-out portions for retaining liquid medicament that leaks along the plunger rod toward the drive mechanism.

13 Claims, 4 Drawing Sheets

(51) Int. Cl.
*A61M 5/24* (2006.01)
*A61M 5/315* (2006.01)
*A61M 15/00* (2006.01)
*A61M 11/00* (2006.01)

(52) U.S. Cl.
CPC ........... *A61M 11/007* (2014.02); *A61M 11/06* (2013.01); *A61M 15/00* (2013.01); *A61M 2005/31523* (2013.01)

(58) Field of Classification Search
CPC .............. A61M 5/2066; A61M 5/2448; A61M 5/281–5/284; A61M 2005/2086; A61M 2005/3101; A61M 2005/31523; A61M 2005/31596; A61M 15/00; A61M 15/0028; A61M 5/24; A61M 5/28; A61M 5/315
See application file for complete search history.

(56) References Cited

U.S. PATENT DOCUMENTS

| | | | |
|---|---|---|---|
| 5,891,087 A * | 4/1999 | Ohtani | A61M 5/284 604/190 |
| D437,050 S * | 1/2001 | Balestracci | D24/112 |
| 6,440,105 B1 | 8/2002 | Menne | |
| 6,565,529 B1 | 5/2003 | Kimber et al. | |
| 6,702,778 B2 * | 3/2004 | Hill | A61M 5/2066 604/82 |
| 8,529,513 B2 * | 9/2013 | Peter | A61M 5/14244 604/131 |
| 2002/0165500 A1 * | 11/2002 | Bechtold | A61M 5/2033 604/209 |
| 2003/0199814 A1 * | 10/2003 | Parsons | A61M 5/30 604/68 |
| 2004/0127858 A1 | 7/2004 | Bendek et al. | |
| 2005/0209569 A1 * | 9/2005 | Ishikawa | A61M 5/20 604/207 |
| 2006/0258988 A1 * | 11/2006 | Keitel | A61M 5/31551 604/181 |
| 2007/0167908 A1 * | 7/2007 | Kirchhofer | A61M 5/2448 604/82 |
| 2009/0308895 A1 * | 12/2009 | Reynolds | A61M 5/2448 222/327 |
| 2010/0160894 A1 * | 6/2010 | Julian | A61M 5/2033 604/506 |
| 2010/0174236 A1 * | 7/2010 | Burns | A61M 5/3202 604/110 |
| 2011/0152781 A1 * | 6/2011 | Brunnberg | A61M 5/3129 604/189 |
| 2011/0213315 A1 | 9/2011 | Sweeney et al. | |
| 2011/0224622 A1 * | 9/2011 | Karlsson | A61M 5/20 604/211 |
| 2012/0136315 A1 * | 5/2012 | Wieselblad | A61M 5/20 604/189 |
| 2012/0209171 A1 * | 8/2012 | Vedrine | A61M 5/284 604/87 |
| 2013/0035642 A1 * | 2/2013 | Daniel | A61M 5/2033 604/189 |
| 2013/0053790 A1 * | 2/2013 | Karlsson | A61M 5/2033 604/218 |
| 2013/0197446 A1 * | 8/2013 | Gustafsson | A61M 5/31595 604/189 |
| 2014/0331996 A1 * | 11/2014 | Elmen | A61M 5/24 128/200.24 |

FOREIGN PATENT DOCUMENTS

| | | |
|---|---|---|
| EP | 0793973 A2 | 9/1997 |
| EP | 0911046 A2 | 4/1999 |
| JP | H10-192403 A | 7/1998 |
| JP | 2005-160888 A | 6/2005 |
| WO | 2007/094833 A1 | 8/2007 |

OTHER PUBLICATIONS

EPO, Written Opinion in PCT/EP2013/054577, dated Jul. 16, 2013, pp. 1-5.

* cited by examiner

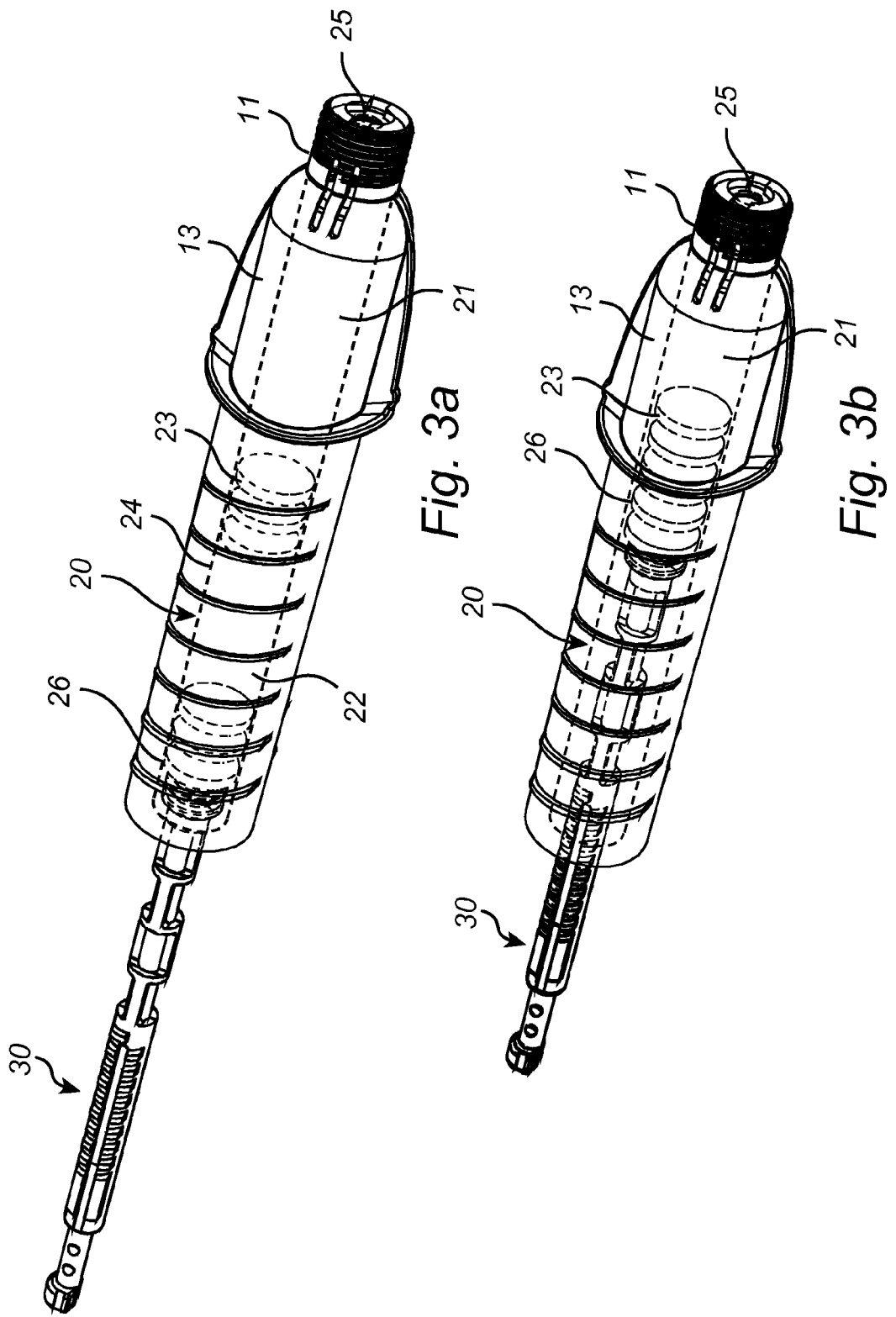

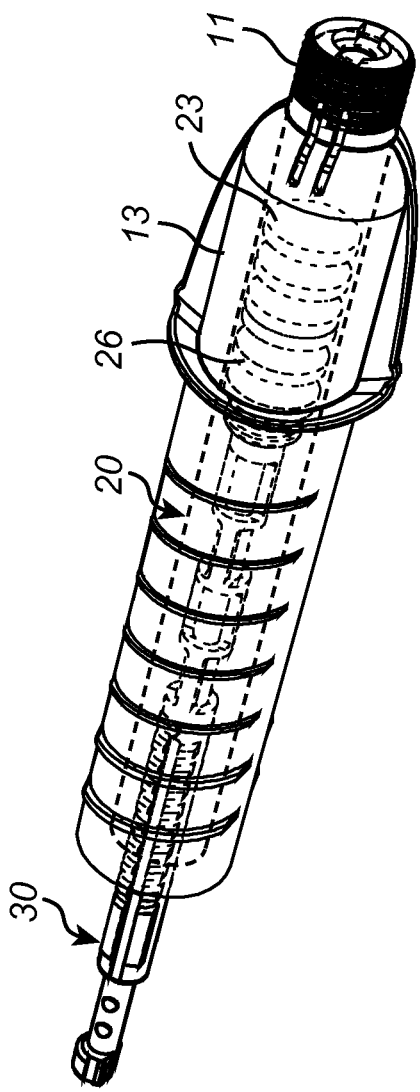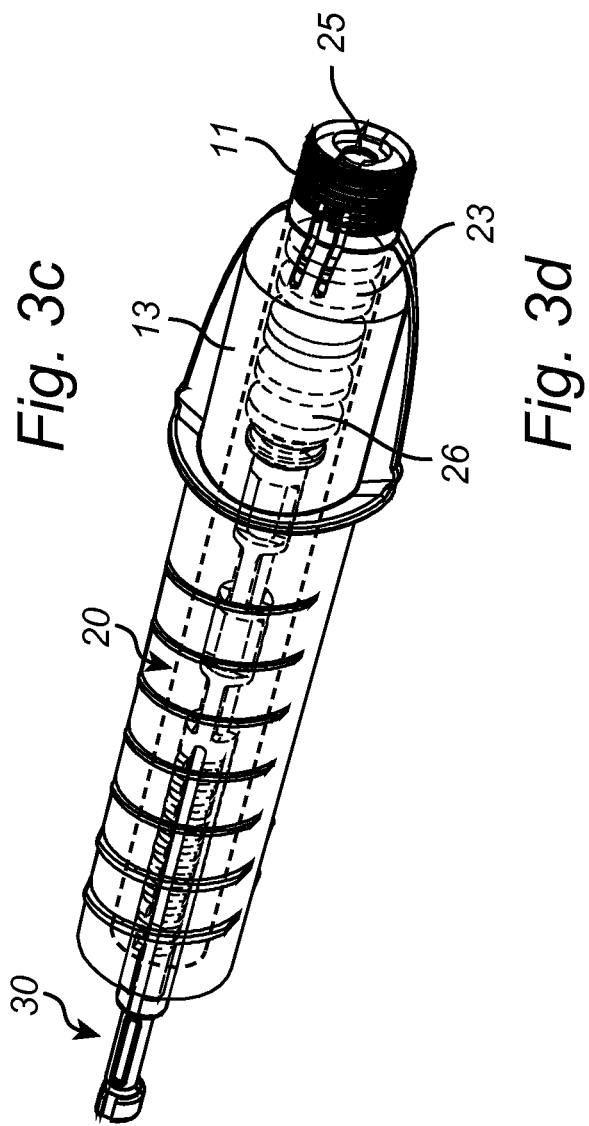

MEDICAMENT DELIVERY DEVICE

FIELD OF THE INVENTION

The present invention relates to an medicament delivery device intended for use in combination with a disposable container.

BACKGROUND OF THE INVENTION

Disposable containers as multi-chamber containers or dual-chamber containers are frequently used in medicament delivery devices in order to facilitate the distribution of drugs to a patient. Dual-chamber containers comprise two longitudinally arranged chambers divided by a movable plunger arranged in the container. In one of chambers, normally the proximal chamber, a predetermined amount of freeze-dried drug is arranged while a diluent is arranged in the distal chamber. When a distal plunger is exposed to a pushing force, the diluent is transferred via a bypass passage to the proximal chamber where the diluent is mixed with the freeze-dried drug. When the distal plunger reaches the dividing proximal plunger, the distal chamber is completely empty and the mixture in the proximal chamber is ready for delivery. Continued proximal movement of the two plungers will deliver the mixture in the proximal chamber via a delivery member i.e. a needle, a nozzle, a mouth piece, etc. to the patient.

Unfortunately, there is a risk that a small amount of the mixture is encapsuled in the bypass passage and may flow back, distally via the bypass passage before the opening of the bypass passage is completely closed by the distal plunger. If the medicament delivery device is held in a vertical position with the delivery member pointing upwards, which is the normal position during preparation of medicament delivery devices i.e. injectors, inhalers, etc. the leaking mixture could continue flowing distally downwards along the plunger rod to the driving mechanism and affect the mechanism adversely. Leakage may sometimes also occur during use of conventional single-chamber containers but not as often as when dual-chamber containers are used.

There is consequently a need for an improved medicament delivery device that can be used over a long period of time together with disposable containers without risking adverse effects from fluids leaking from the containers.

SUMMARY OF THE INVENTION

The present invention, defined in the appended claims, provides a medicament delivery device that fulfils the needs defined above.

The medicament delivery device according to the invention is elongated along a longitudinal axis (A), has a proximal end and a distal end. Said device is intended for use in combination with a disposable container which comprises at least one chamber for a liquid medicament encapsulated in the container by at least one movable plunger, said device comprises:
- an elongated plunger rod configured to be in contact with the at least one movable plunger;
- a drive mechanism configured to, when the medicament delivery device is activated, apply a force in a proximal direction via said plunger rod acting on said at least one movable plunger;
- an elogated housing comprising a proximal housing section and a distal housing section, said proximal housing section being configured to accommodate the container and said distal housing section being configured to accommodate the plunger rod and the driving mechanism. Said elongated plunger rod comprises an outer periphery in which at least two axially separated recesses and/or cut-out portions are arranged for retaining leaking liquid medicament that may flow along the plunger rod to the drive mechanism.

The claimed invention fulfils the needs defined above since fluid leaking from the container is trapped in the recesses and/or cut-out portions in the plunger rod and is thereby prevented from reaching the drive mechanism in the distal end of the medicament delivery device.

In one embodiment of the invention, the disposable container is a multi-chamber medicament container comprising a proximal chamber wherein an active medicament is encapsulated, a distal chamber wherein a diluent is encapsulated, a passage between the chambers, a proximal movable plunger sealing the proximal chamber and the passage, and a distal movable plunger sealing the distal chamber. The proximal end of elongated plunger rod is configured to be in contact with the distal movable plunger.

In one embodiment of the invention, the device is configured such that when a force is exerted on said distal movable plunger by the plunger rod which is driven by the drive mechanism, said distal and proximal plungers are forced to move towards the proximal end of the device such that the diluent may flow through the passage for being mixed with the active medicament forming a liquid medicament.

In one embodiment of the invention, a spinner is arranged rotatable around the longitudinal axis and in relation to the plunger rod, at the proximal end of said plunger rod, said spinner having an outer periphery also provided with one, or more, recesses and/or cut-out portions. This embodiment is favourable since recesses and/or cut-out portions of the spinner are located close to the movable plunger and the inner periphery of the container and will provide a first efficient trap for leaking fluid.

In one embodiment of the invention, the axially separated recesses and/or cut-out portions of the plunger rod are arranged at different locations around the outer periphery of the plunger rod. This embodiment provides an even more efficient trap for the liquid since the different locations of the recesses and/or cut-out portions will reduce the risk that leaking fluid is able to continue along the plunger rod between adjacent recesses and/or cut-out portions.

In one embodiment of the invention, said at least two recesses and/or cut-out portions in said plunger rod extend a radial distance from the outer periphery of the plunger rod towards the longitudinal axis (A) that is less then the radius of the plunger rod in the area of the recess or cut-out portion. This embodiment is favourable since the center of the plunger will remain solid through the entire plunger rod. This ensures that the plunger rod will have the required axial strength to withstand the force applied by the drive mechanism on the plunger rod.

In one embodiment of the invention, said recesses and/or cut-out portions in the plunger rod and/or spinner are filled with a liquid-absorbing material. This embodiment further improves the posibillity for the plunger rod to absorb and maintain the leaking fluid in the recesses and/or cut-out portions.

In one embodiment of the invention, the peripheral width of said recesses and/or cut-out portions in the plunger rod exceeds half the peripheral width of the plunger rod in the area of the recesses and/or cut-out portions. This embodiment is favourable since larger recesses and/or cut-out portions will increase the possibilities of preventing fluid from continuing along the plunger rod.

The medicament delivery device is an injector or an inhaler.

The different embodiments described above could of course be combined and modified in different ways without departing from the scope of the invention that is defined by the claims. Further aspects of the invention will be described more in detail in the detailed description.

BRIEF DESCRIPTION OF THE DRAWINGS

One embodiment of the present invention is illustrated in the appended figures disclosing:

FIG. 3a illustrates the proximal housing section before fluid in the second chamber of the container is mixed with the drug in the first chamber of the container.

FIG. 3b illustrates the proximal housing section and the container after mixing, ready for use.

FIG. 3c illustrates the position of the plunger rod when the medicament delivery has been started but not ended.

FIG. 3d illustrates the plunger rod and the container once the medicament delivery is completed.

DETAILED DESCRIPTION

Figure 1:
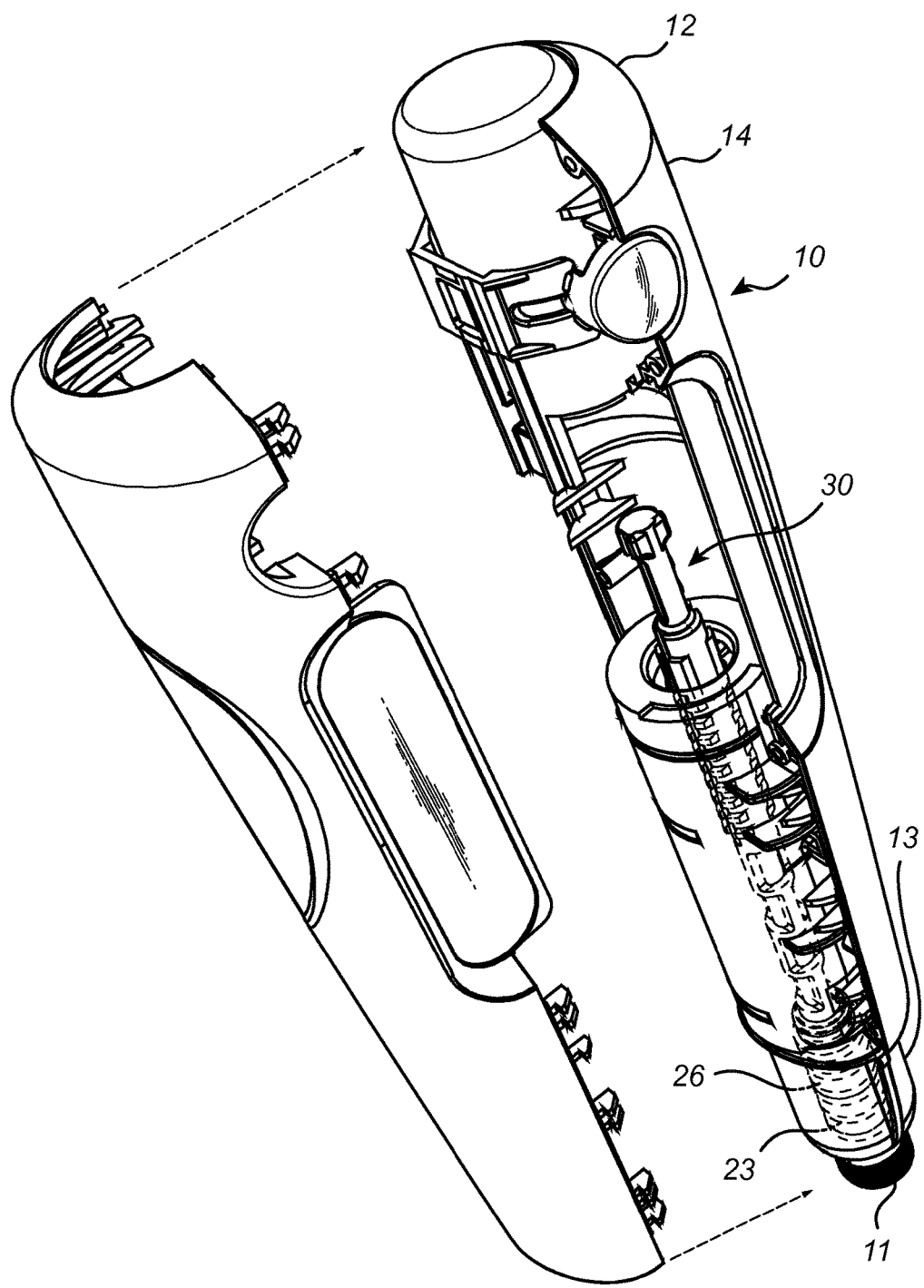
FIG. 1 is an exploded perspective side view.
Figure 2:
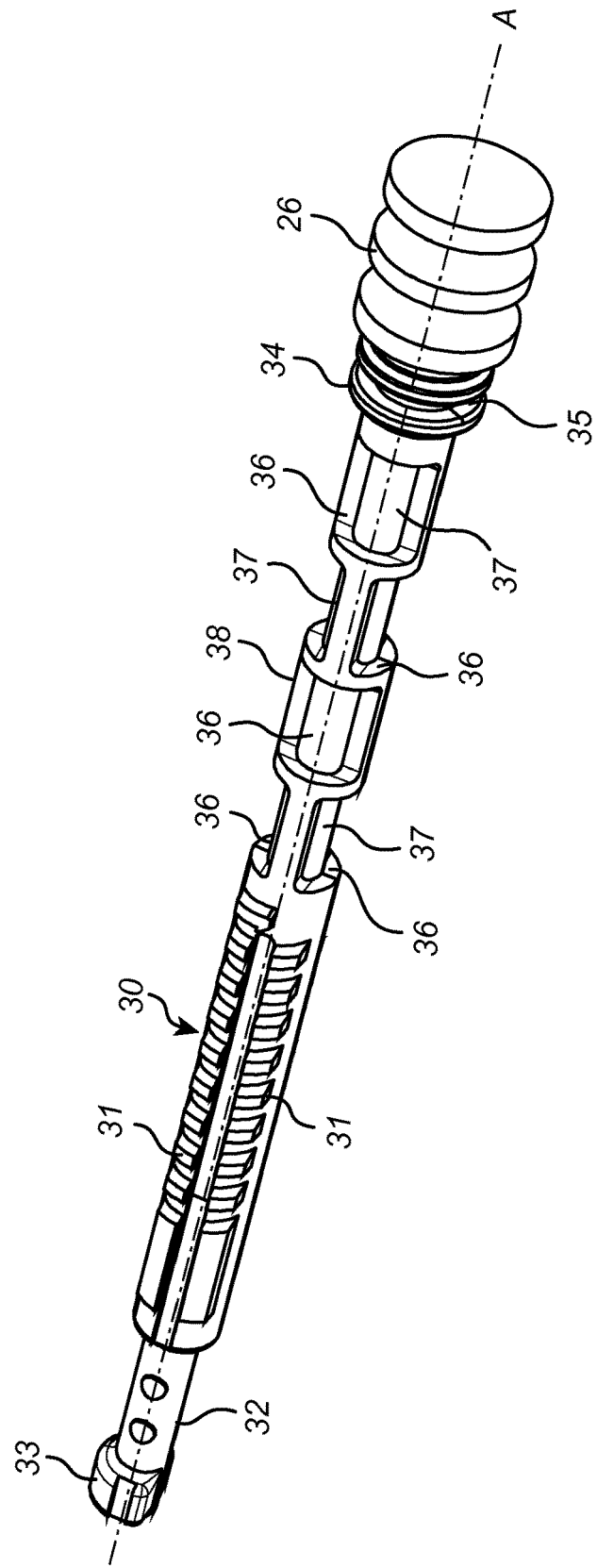
FIG. 2 illustrates the plunger rod according to the invention.

In FIG. 1, one embodiment of an medicament delivery device according to the present invention is schematically illustrated in an exploded perspective view in order to illustrate the different components of the medicament delivery device 10. The medicament delivery device 10 is mostly intended for self administration of a drug by a patient. The medicament delivery device 10 comprises a protective elongated housing having a proximal 11 and distal end 12, and a longitudinal axis (A). The medicament delivery device housing is divided in a proximal housing section 13 and a distal housing section 14 that during the assembly of the medicament delivery device 10 are removably attached to each other. The medicament delivery device 10 furthermore comprises a movable plunger rod 30 driven by a drive mechanism, not illustrated, arranged in the distal housing section 14. The medicament delivery device 10 is intended for use in combination with disposable containers 20, preferably disposable multi-chamber containers, that during the assembly of the medicament delivery device 10 are arranged in the proximal housing section 13.

Within the proximal housing section 13, a space is defined in order to house the disposable container 20. The disposable container 20 is either a dual chamber container, as illustrated in the FIGS. 3a-3d, or a conventional one-chamber container. The container 20 comprises a container vessel 24 normally made of glass and sealed in the proximal end by an elastic sealing member 25. The elastic sealing member 25 is punctuated by a delivery member i.e. a needle, not illustrated in the figures, when the medicament delivery device 10 is prepared for use. The container is sealed by a distal movable plunger 26 at the distal end of the container vessel in order to seal the container. The illustrated container is a dual-chamber container, illustrated for example in FIGS. 3a to 3d. Dual-chamber containers comprise two longitudinally arranged chambers, a proximal chamber 21 and a distal chamber 22, divided by a proximal movable plunger 23 arranged in the container. When the medicament delivery device 10 is activated and prepared for use, the distal plunger 26 is moved in the proximal direction by the movable plunger rod 30 which is driven by the drive mechanism such that a diluent from the distal chamber 22 is transferred via a bypas passage to the proximal chamber 21 whereby the diluent is mixed with a freeze-dried drug, FIG. 4b, forming a liquid medicament. When the distal plunger 26 reaches the proximal plunger 23, the distal chamber 22 is emptied completely and the mixture in the proximal chamber 21 is ready for use.

Continued distal movement of the plungers 26 and 23 will deliver the liquid medicament in the proximal chamber 21, FIG. 3c, to the patient via a non-illustrated delivery member arranged at the proximal end 11 of the housing.

Preparation of the medicament delivery device is done by moving, e.g. by turning, the proximal housing section 13 and the distal housing section 14 in relation to each other. The turning movement will, due to the threads on the outside of the proximal housing section and corresponding threads on the inside surface of the distal housing section, move the distal housing section, and the plunger rod, towards the proximal housing section and transfer the diluent in the distal chamber 22 to the proximal chamber 21 of the container 20, thereby mixing the constituents of the two chambers. Preparation can also be achieved by the drive mechanism that generates a first force in the proximal direction of the medicament delivery device 10. The first force is transferred from the drive mechanism to the plungers 26 and 23 via the elongated plunger rod 30.

The drive mechanism (not illustrated), is of conventional type used in this type of medicament delivery devices. The drive mechanism is configured to generate the movement of the plunger rod 30 e.g. by co-operation with external threads 31 arranged around the outer periphery of the plunger rod in the distal end of the plunger rod 30. The distal end of the plunger rod has a thinner section 32 and a protrusion 33 configured to engage with corresponding components of the drive mechanism. In the proximal end of the plunger rod 30 a spinner 34, rotatable around the axis A, is arranged to abut the distal plunger 26. The spinner 34 is advantageous since the drive mechanism generates a turning movement of the plunger rod 30 and the rotatable spinner 34 reduces the friction that otherwise would occur been between the first plunger 26 and the proximal end of the plunger rod 30. The spinner 34 has a circular cross section, viewed along the axis A, with a slightly smaller radius than the distal plunger 26 in order to not be in contact with the inner periphery of the container. The outer periphery of the spinner 34 is furthermore provided with an annular groove 35 extending around the entire periphery of the spinner 34 in order to house leaking fluid from the container and to prevent the fluid from flowing along the plunger rod 30 in the distal direction towards the drive mechanism.

Between the spinner 34 and the threads 31 the plunger rod 30 is provided with a number of cut-out portions 36. The cut-out portions 36 are axially separated along the plunger rod 30 in order to efficiently prevent that leaking fluid flows along the plunger rod 30 without interruption. The cut out portions should be axially separated in order to prevent the fluid from flowing between the cut-out portions towards the drive mechanism in the distal end of the medicament delivery device.

Each cut-out portion 36 has a depth that is less than the radius of the plunger rod in the area of the cut-out portion in order to ensure that enough material remains in a plunger rod core to be able to withstand drive forces of the drive mechanism exerted on the plunger rod upon activation of the device. In order to ensure sufficient axial strength of the plunger rod the illustrated embodiment of the plunger rod has a central core 37 with a circular cross section in which no cut-out portions are arranged.

Each cut-out portion has a peripheral width that is less than half of the outer periphery of the plunger rod in order to make room for identical cut-out portions 36 on opposite sides of the plunger rod. The peripheral width of the cut-out portions could however be increased up to the entire periphery of the plunger rod. Preferably the total peripheral width of the cut-out portions exceed half the total peripheral lenght of the plunger rod in the area of the cut-out portions in order to provide efficient fluid traps and to ensure that the fluid will end up in the cut-out portions instead of flowing along the plunger rod between said cut-out portions.

In the appended figures, one embodiment of cut-out portions is illustrated. The design of the cut-out portions could however be modified in a number of different ways. For example the number and size of the cut-out portions could be changed or the cut-out portions could be replaced by recesses distributed over the outer periphery of the plunger rod. The recesses could for example have a spherical shape, round shape, holes extending through the plunger rod as long as enough material remains on the side of the holes, annular grooves around the outer periphery of the plunger rod etc. Furthermore different types of recesses and/or cut-out portions could be used in combination.

A further advantageous embodiment is achieved if the cut-out portions or recesses are filled by a fluid absorbing material that is able to absorb fluid flowing along the plunger rod and to ensure that the fluid is retained by the recesses and/or cut-out portions.

Even though different embodiments of the medicament delivery device according to the invention have been described, the invention is not limited to the disclosed embodiments that could be modified further, for example: the number, size, and shape of the cut-out portions could be changed as well as the design of the injector device.

The invention claimed is:

1. A medicament delivery device for a disposable container having at least one chamber for a liquid medicament encapsulated in the container by at least one movable plunger, the medicament delivery device being elongated along a longitudinal axis, having a proximal end and a distal end, and comprising:
    a plunger rod configured for contacting the at least one movable plunger;
    a drive mechanism configured for applying a force in a proximal direction via the plunger rod on the at least one movable plunger when the medicament delivery device is activated; and
    a housing, comprising a proximal housing section configured for accommodating the disposable container and a distal housing section configured for accommodating the plunger rod and the drive mechanism;
    wherein the plunger rod comprises an outer periphery having at least two axially separated recesses or cut-out portions configured for retaining liquid medicament that leaks along the plunger rod toward the drive mechanism; and the axially separated recesses or cut-out portions are filled with a liquid absorbing material.

2. The medicament delivery device of claim 1, wherein the disposable container is a multi-chamber medicament container, comprising a proximal chamber for encapsulating an active medicament, a distal chamber for encapsulating a diluent, a passage between the proximal and distal chambers, a proximal movable plunger configured for sealing the proximal chamber and the passage, and a distal movable plunger configured for sealing the distal chamber; and the proximal end of the plunger rod is configured for contacting the distal movable plunger.

3. The medicament delivery device of claim 2, wherein when a force is exerted on the distal movable plunger by the plunger rod driven by the drive mechanism, the distal and proximal movable plungers are forced to move toward the proximal end of the medicament delivery device such that diluent flows through the passage for mixing with the active medicament, thereby forming the liquid medicament.

4. The medicament delivery device of claim 1, wherein the axially separated recesses or cut-out portions are arranged at different locations around an outer periphery of the plunger rod.

5. The medicament delivery device of claim 4, wherein an axially separated recess or cut-out portion extends a radial distance from the outer periphery of the plunger rod toward the longitudinal axis that is less than a radius of the plunger rod in an area of the recess or cut-out portion.

6. The medicament delivery device of claim 1, wherein peripheral widths of the axially separated recesses or cut-out portions exceed half a peripheral width of the plunger rod in an area of the recesses or cut-out portions.

7. The medicament delivery device of claim 1, wherein the medicament delivery device is an injector or an inhaler.

8. A medicament delivery device for a disposable container having at least one chamber for a liquid medicament encapsulated in the container by at least one movable plunger, the medicament delivery device being elongated along a longitudinal axis, having a proximal end and a distal end, and comprising:
    a plunger rod configured for contacting the at least one movable plunger;
    a drive mechanism configured for applying a force in a proximal direction via the plunger rod on the at least one movable plunger when the medicament delivery device is activated;
    a housing, comprising a proximal housing section configured for accommodating the disposable container and a distal housing section configured for accommodating the plunger rod and the drive mechanism; and
    a spinner rotatably arranged around the longitudinal axis and in relation to the plunger rod at a proximal end of the plunger rod, the spinner having an outer periphery provided with at least one recess or cut-out portion,
    wherein the plunger rod comprises an outer periphery having at least two axially separated recesses or cut-out portions configured for retaining liquid medicament that leaks along the plunger rod toward the drive mechanism.

9. The medicament delivery device of claim 8, wherein the axially separated recesses or cut-out portions of the plunger rod are arranged at different locations around an outer periphery of the plunger rod.

10. The medicament delivery device of claim 9, wherein an axially separated recess or cut-out portion of the plunger rod extends a radial distance from the outer periphery of the plunger rod toward the longitudinal axis that is less than a radius of the plunger rod in an area of the axially separated recess or cut-out portion.

11. The medicament delivery of claim 8, wherein at least one of the axially separated recesses or cut-out portions of the plunger rod and the recess or cut-out portion of the spinner are filled with a liquid absorbing material.

12. The medicament delivery device of claim 8, wherein peripheral widths of the axially separated recesses or cut-out portions of the plunger rod exceed half a peripheral width of the plunger rod in an area of the recesses or cut-out portions.

13. The medicament delivery device of claim 8, wherein the medicament delivery device is an injector or an inhaler.

\* \* \* \* \*